(12) United States Patent
Marciano et al.

(10) Patent No.: US 6,648,843 B1
(45) Date of Patent: Nov. 18, 2003

(54) COMBINATION NIGHT SPLINT AND WALKING BOOT

(75) Inventors: Paul Thomas Marciano, Keller, TX (US); Jimmy Wayne Ketner, Grand Prairie, TX (US)

(73) Assignee: MK, L.L.P., Grapevine, TX (US)

( * ) Notice: Subject to any disclaimer, the term of this patent is extended or adjusted under 35 U.S.C. 154(b) by 0 days.

(21) Appl. No.: 10/390,267

(22) Filed: Mar. 17, 2003

(51) Int. Cl.$^7$ .................................................. A61F 5/00
(52) U.S. Cl. ............................................. 602/27; 602/3
(58) Field of Search ............................. 602/27, 28, 65, 602/3, 66, 62, 61, 23, 5, 16; 36/15, 7.5, 117.3

(56) References Cited

U.S. PATENT DOCUMENTS

| | | | | |
|---|---|---|---|---|
| 3,802,424 A | * | 4/1974 | Newell | 602/3 |
| 4,005,704 A | | 2/1977 | Stöhr et al. | |
| 4,094,312 A | * | 6/1978 | Whyte | 602/10 |
| 4,567,678 A | * | 2/1986 | Morgan et al. | 36/110 |
| 4,771,768 A | * | 9/1988 | Crispin | 602/16 |
| 4,962,760 A | * | 10/1990 | Jones | 602/27 |
| 4,974,583 A | * | 12/1990 | Freitas | 602/24 |
| 5,094,232 A | | 3/1992 | Harris et al. | |
| 5,176,623 A | | 1/1993 | Stetman et al. | |
| 5,250,021 A | * | 10/1993 | Chang | 602/27 |
| 5,464,385 A | * | 11/1995 | Grim | 602/27 |
| 5,571,078 A | * | 11/1996 | Malewicz | 602/27 |
| 5,609,570 A | | 3/1997 | Lamont | |
| 5,611,773 A | * | 3/1997 | Nash et al. | 602/16 |
| 5,620,411 A | * | 4/1997 | Schumann et al. | 602/23 |
| 5,797,865 A | | 8/1998 | McDavid, III | |
| 5,827,207 A | | 10/1998 | MacMorran | |
| 5,897,520 A | | 4/1999 | Gerig | |
| 5,913,841 A | * | 6/1999 | Lamont | 602/65 |
| 6,146,350 A | | 11/2000 | Morton | |
| 6,155,998 A | * | 12/2000 | Gilmour | 602/27 |

OTHER PUBLICATIONS

Thomas et al., *The Diagnosis and Treatment of Heel Pain*, The Journal of Foot & Ankle Surgery, Sep./Oct. 2001, vol. 40, No. 5.

*Effective Treatment of Chronic Plantar Fasciitis with Dorsiflexion Night Splints: A Crossover Prospective Randomized Outcome Study*, Foot & Ankle International, 1998, American Orthopaedic Foot and Ankle Surgery, Inc.

Angela Evans, *Podiatric Medical Applications of Posterior Night Stretch Splinting*, Journal of the American Podiatric Medical Association, Jul./Aug. 2001, vol. 91, No. 7.

Keith Wapner and Peter Sharkley, *The Use of Night Splints for Treatment of Recalcitrant Plantar Fasciitis*, Foot & Ankle, Dec. 1991, vol. 12, No. 3, American Orthopaedic Foot and Ankle Surgery, Inc.

A. Louis Jimenez and Robert Goecker, *Night Splints: Conservative Management of Plantar Fasciitis*, Biomechanics, Sep. 1997, Miller Freeman, Inc.

Barry et al., *A Retrospective Study of Standing Gastrocnemius–Soleus Stretching Versus Night Splinting in the Treatment of Plantar Fasciitis*, The Journal of Foot & Ankle Surgery, Jul./Aug. 2002, vol. 41, No. 4, American Orthopaedic Foot and Ankle Surgery, Inc.

* cited by examiner

Primary Examiner—Nicholas D. Lucchesi
Assistant Examiner—Huong Q. Pham
(74) Attorney, Agent, or Firm—Andrew J. Dillon; Bracewell & Patterson, L.L.P.

(57) ABSTRACT

A frequent method of treating Plantar Fasciitis, acute ankle sprains, Achilles tendon repairs, foot drop or other conditions is a so-called night splint which may be utilized by a patient while sleeping, or during other period of extended inactivity, to maintain a desired orientation between a patient's foot and lower leg. A night splint portion includes a thin, lightweight sole portion not suitable for walking or other weight bearing activities; however, a sturdy raised lip around the sole portion includes multiple mounting slots which temporarily mate with matching mounting tabs on a walking boot attachment which includes a sturdy weight bearing sole so that a patient may temporarily convert the night splint to a walking boot.

11 Claims, 6 Drawing Sheets

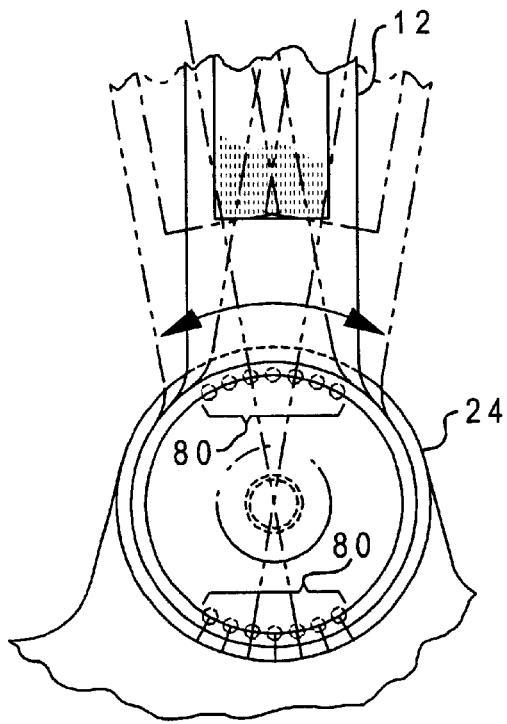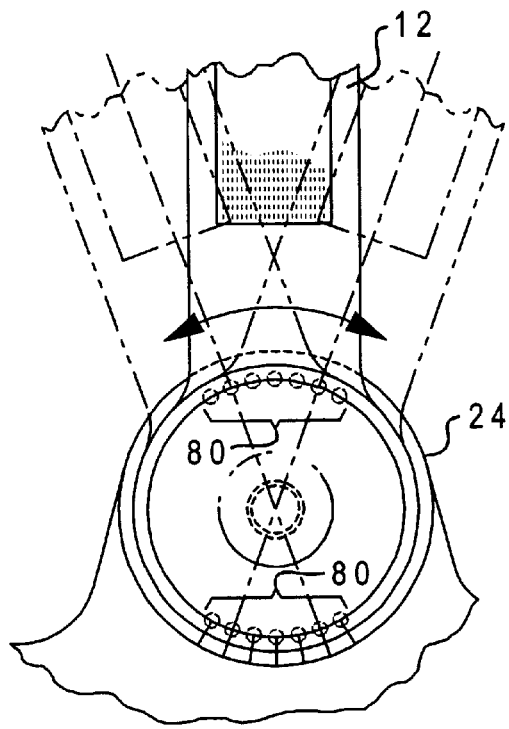
Fig. 6A
Fig. 6B
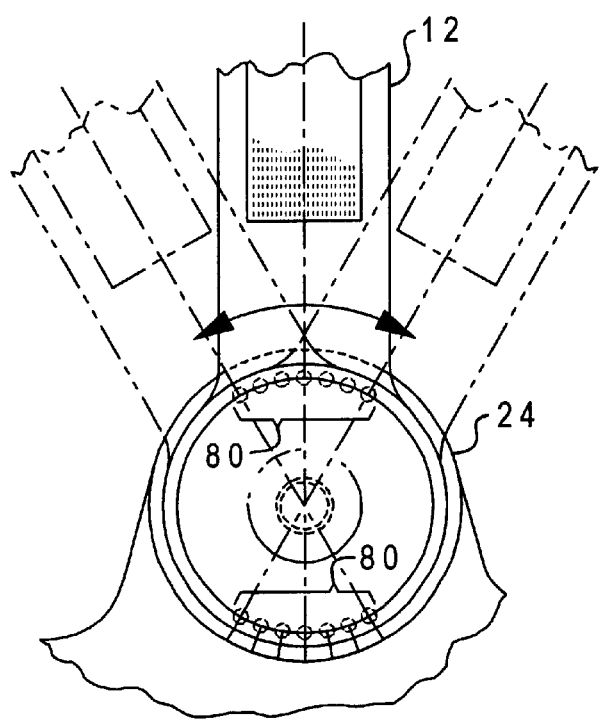
Fig. 6C

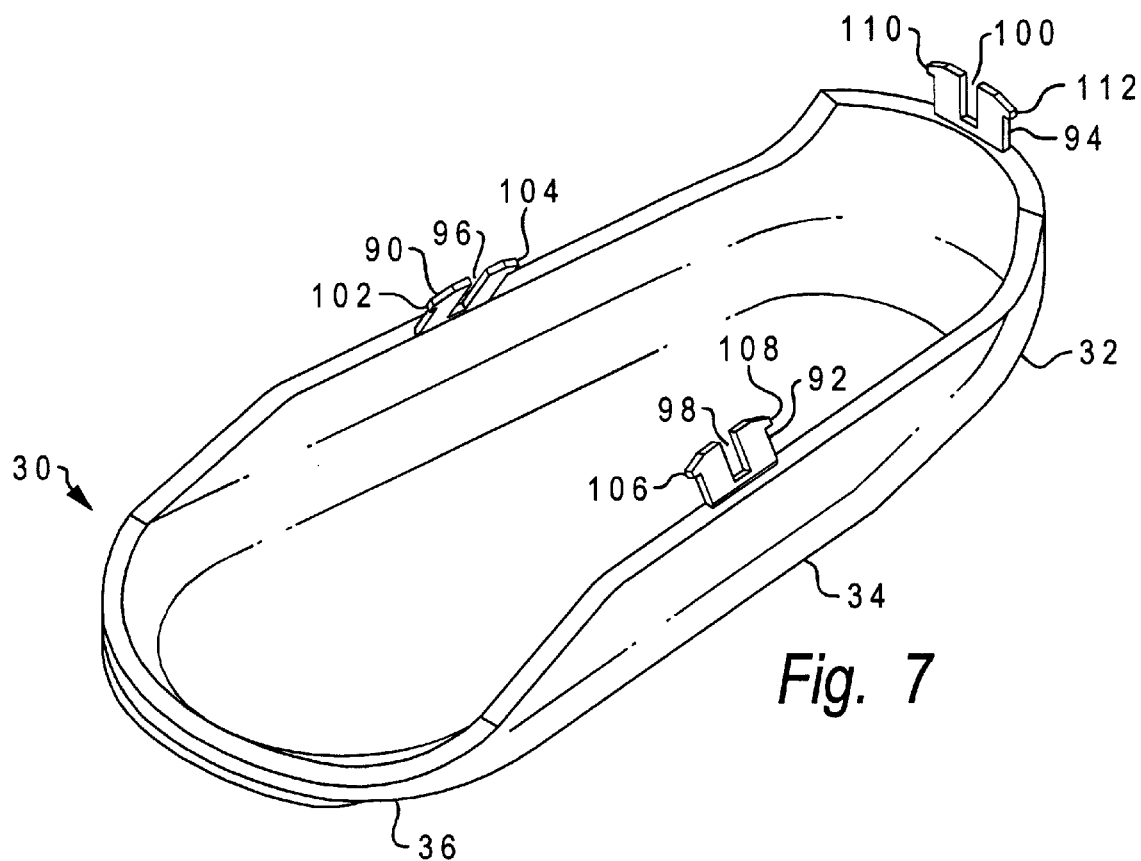
Fig. 7
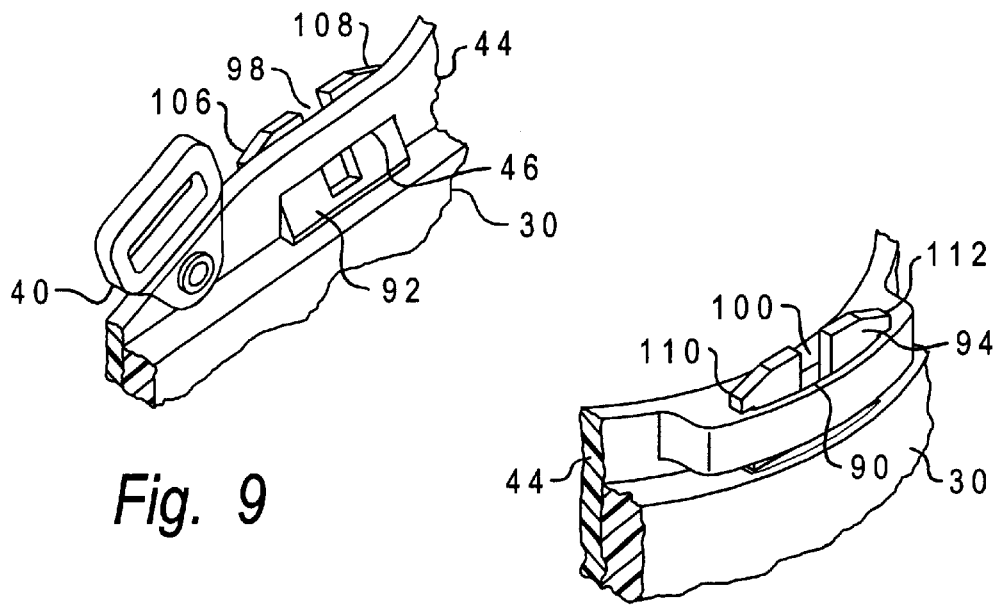
Fig. 9
Fig. 10

COMBINATION NIGHT SPLINT AND WALKING BOOT

BACKGROUND OF THE INVENTION

1. Field of the Invention

The present invention relates in general to a treatment for a Plantar Fasciitis, acute ankle sprains, tendonitis, tendon ruptures, acute foot pain, or other conditions and in particular to a splint or boot for immobilizing the human foot and ankle. Still more particularly, the present invention relates to a night splint for stretching ankle tendons, which can be converted to a durable walking boot with minimal complexity.

2. Description of the Prior Art

In the area of orthotic splints, the prior art has generally evolved into two distinct designs, walking boots and splints.

Walking boots are generally study, heavy and designed to support the patients weight during walking or other ambulatory activities. Examples of walking boots may be seen in U.S. Pat. No. 5,611,773, U.S. Pat. No. 4,962,760 and U.S. Pat. No. 5,176,623. Each of these devices is designed to restrict the flexing of the human foot with respect to the lower leg and frequently such boots include adjustable hinge mounts so that the amount of Dorsi flexion or Plantar flexion may be accurately described and controlled.

Splints on the other hand are typically lightweight and designed to be worn while the patient sleeps or during other periods of extended inactivity. Examples of splints may be seen in U.S. Pat. No. 5,797,865, U.S. Pat. No. 6,146,350, U.S. Pat. No. 5,897,520 and U.S. Pat. No. 5,094,232. Each of these splints is lightweight and designed to be worn either with a conventional shoe or, alternatively, while the patient sleeps or during an extended period of inactivity.

This dichotomy between the two design philosophies has resulted in some difficulty for patients whose medical treatment requires that the movement of their foot or ankle be restricted during long periods of time, but who cannot sleep with a heavy durable walking splint in place or cannot walk while wearing a lightweight night splint. A similar problem had existed when the ankle is immobilized utilizing a plaster or fiberglass cast. Recognizing this difficulty, several inventors have attempted to provide cast protective devices, which could be slipped over the foot portion of a plaster or fiberglass cast to protect the cast while permitting the wearer some degree of mobility. Excellent examples of these devices may be seen in U.S. Pat. No. 3,802,424 and U.S. Pat. No. 4,005,704.

The desirability of a lightweight night splint which may be modified to permit the patient to become ambulatory is known in the art. U.S. Pat. No. 5,913,841, issued to William D. Lamont, discloses a medical boot which includes a lightweight night splint device and which includes a durable fabric material which may be temporarily attached to the bottom of the boot to permit some ambulation on the part of the patient. Similarly, U.S. Pat. No. 5,609,570 issued to the same inventor, discloses a boot, which may be wrapped around the night splint and patients ankle to permit the user to ambulate while wearing a night splint.

Upon reference to these last two patents, it should be apparent that while providing an excellent solution to the problem of ambulation while wearing a lightweight night splint, neither of these designs provides anywhere near the weight bearing durability of typical walking boot splints and consequently, it would be desirable to provide a method or system whereby a lightweight night splint may be efficiently converted to a walking boot without undue complexity.

SUMMARY OF THE INVENTION

It is therefore one object of the present invention to provide an improved treatment for Plantar Fasciitis, acute ankle sprains, tendonitis, tendon ruptures, acute foot pain, or other conditions.

It is another object of the present invention to provide an improved splint for immobilizing the human foot and ankle.

It is yet another object of the present invention to provide a splint for stretching ankle tendons during periods of inactivity, which can be converted to a walking boot with minimal complexity.

The foregoing objects are achieved as is now described. A frequent method of treating Plantar Fasciitis, acute ankle sprains, tendonitis, tendon ruptures, acute foot pain, or other conditions is a so-called night splint which may be utilized by a patient while sleeping, or during other periods of extended inactivity, to maintain a desired orientation between a patient's foot and lower leg, thus stretching ankle tendons. A night splint portion includes a thin, lightweight sole portion not suitable for walking or other weight bearing activities; however, a sturdy raised lip around the sole portion includes multiple mounting slots which temporarily mate with matching mounting tabs on a walking boot attachment which includes a sturdy, weight bearing sole so that a patient may temporarily convert the night splint to a walking boot.

BRIEF DESCRIPTION OF THE DRAWINGS

The novel features believed characteristic of the invention are set forth in the appended claims. The present invention itself, however, as well as a preferred mode of use, further objectives, and advantages thereof, will best be understood by reference to the following detailed description of a preferred embodiment when read in conjunction with the accompanying drawings, wherein:

FIGS. 6A–6C are schematic views of the rotatable hinge of FIG. 3, demonstrating the range of adjustment possible;

FIG. 7 is a perspective view of the walking boot portion of the combination night splint and walking boot of the present invention;

FIGS. 9 and 10 are partial views of the mounting slots and tabs utilized to join the night splint portions and walking boot portions of the present invention.

DETAILED DESCRIPTION OF THE PREFERRED EMBODIMENT

Figure 1:
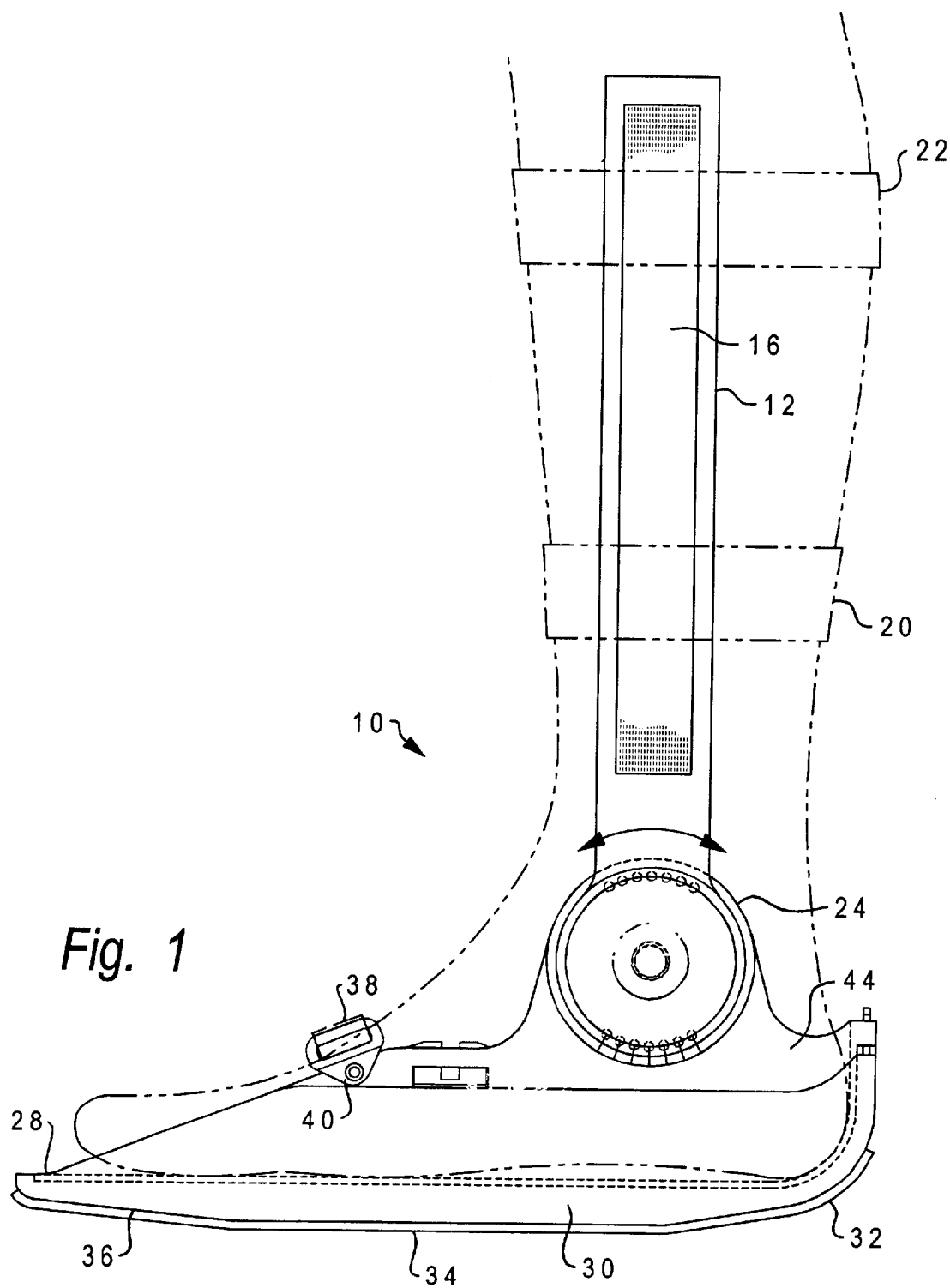
FIG. 1 is a side pictorial view of the combination night splint and walking boot of the present invention.

With reference now to the Figures and in particular with reference to FIG. 1, there is illustrated a side pictorial view of the combination night splint and walking boot 10 of the present invention. As illustrated, combination night splint and walking boot 10 is constructed of a lightweight material such as Titanium, Aluminum or Plastic, such as Nylon Polyurethane or Polyethylene and includes a leg brace 12 and an identical second leg brace 14 (not shown in this Figure). Mounted along leg brace 12 is a hook or loop fastener strip 16 and a similar strip is provided on the opposite leg brace. In this manner, a pair of hook or loop straps 20 and 22 may be wrapped around the lower leg of the patient and, when engaged with the hook or loop strip 16 and the second hook or loop strip, may be utilized to retain the pair of leg braces in a tight proximate position to the lower leg of the patient.

Mounting each leg brace 12 or 14 to combination night splint and walking boot 10 is a rotatable hinge 24. A similar rotatable hinge 26 is also provided but not depicted in this Figure.

A foot support member 28 is provided and, as illustrated, is constructed utilizing a thin flat sole portion, which may be utilized to support the human foot. A walking boot attachment 30 is mounted to foot support member on 28 and includes a heel portion 32, mid-foot portion 34, and a toe portion 36. As illustrated in FIG. 1, heel portion 32 and toe portion 36 are slightly inclined from the plane defined by mid-foot portion 34 in order to assist the patient in walking.

An instep strap 38 is illustrated which is attached to turnbuckles 40 and 42 (not shown in this Figure) and utilized to further restrain the human foot in close proximity to foot support member 28. Finally, as illustrated in FIG. 1, a raised lip portion 44 is depicted. As illustrated, raised lip portion 44 forms a counter around the heel area of combination night splint and walking boot 10 and extends along each side of foot support member 28, forming the mounting surface for turnbuckles 40 and 42 (not shown in this Figure).

Figure 2:
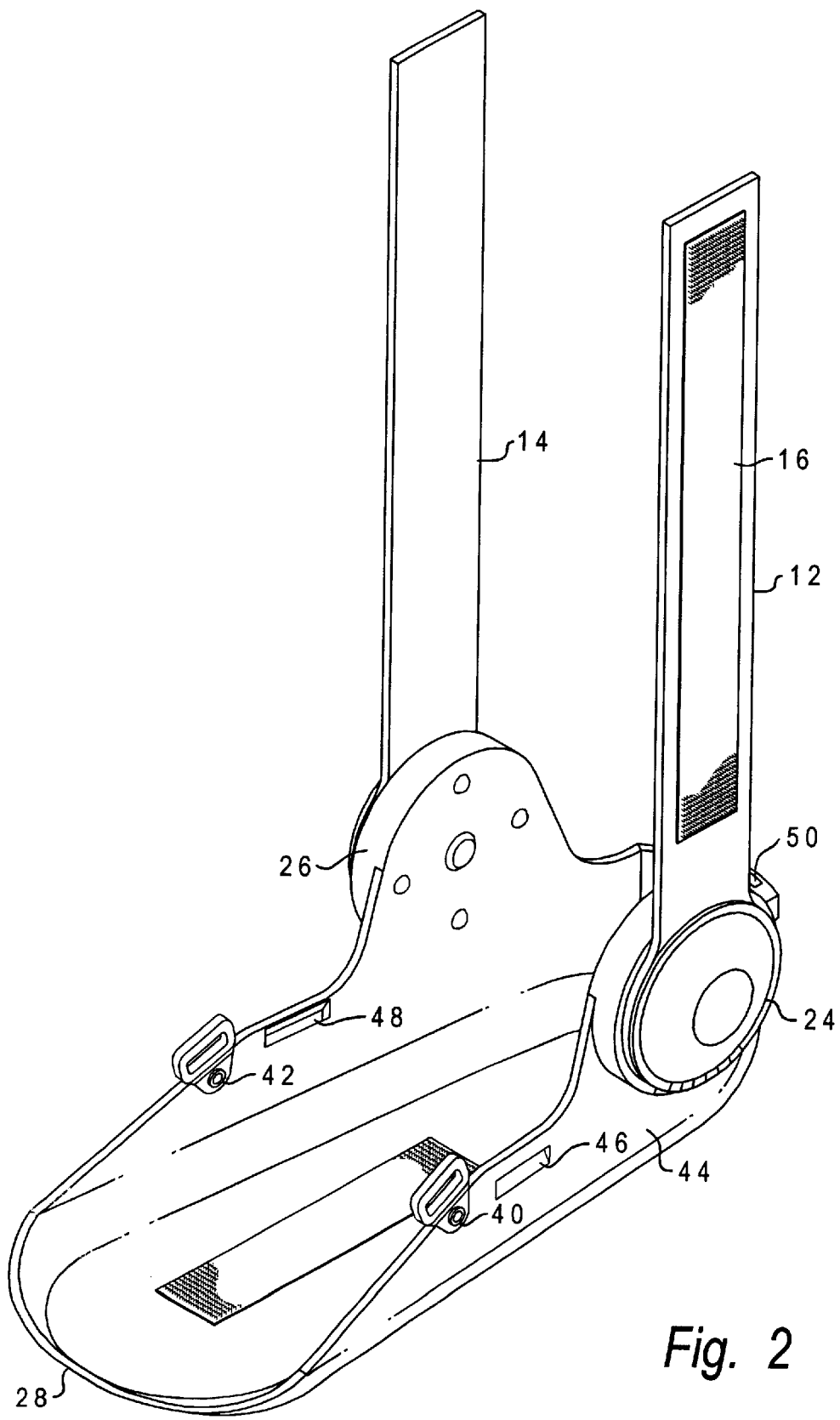
FIG. 2 is a perspective view of the night splint portion of the combination night splint and walking boot of the present invention.

Referring now to FIG. 2, there is depicted a perspective view of the night splint portion of the combination night splint and walking boot of the present invention. As now depicted, leg braces 12 and 14 extend upward along the lower leg of the patient and are mounted to foot support member 28 by means of rotatable hinges 24 and 26.

As clearly illustrated herein, raised lip portion of 44 forms a counter around the heel area of foot support member 28 and extends along each side thereof, providing a mounting surface for turnbuckles 40 and 42.

In accordance with an important feature of the present invention, raised lip portion 44 also serves to provide a plurality of mounting slots. Generally rectangular mounting slots 46, 48 and 50 are depicted in FIG. 2; however, those ordinarily skilled in the art will appreciate, upon reference to the foregoing, that a greater or lesser number of slots maybe chosen.

Figure 3:
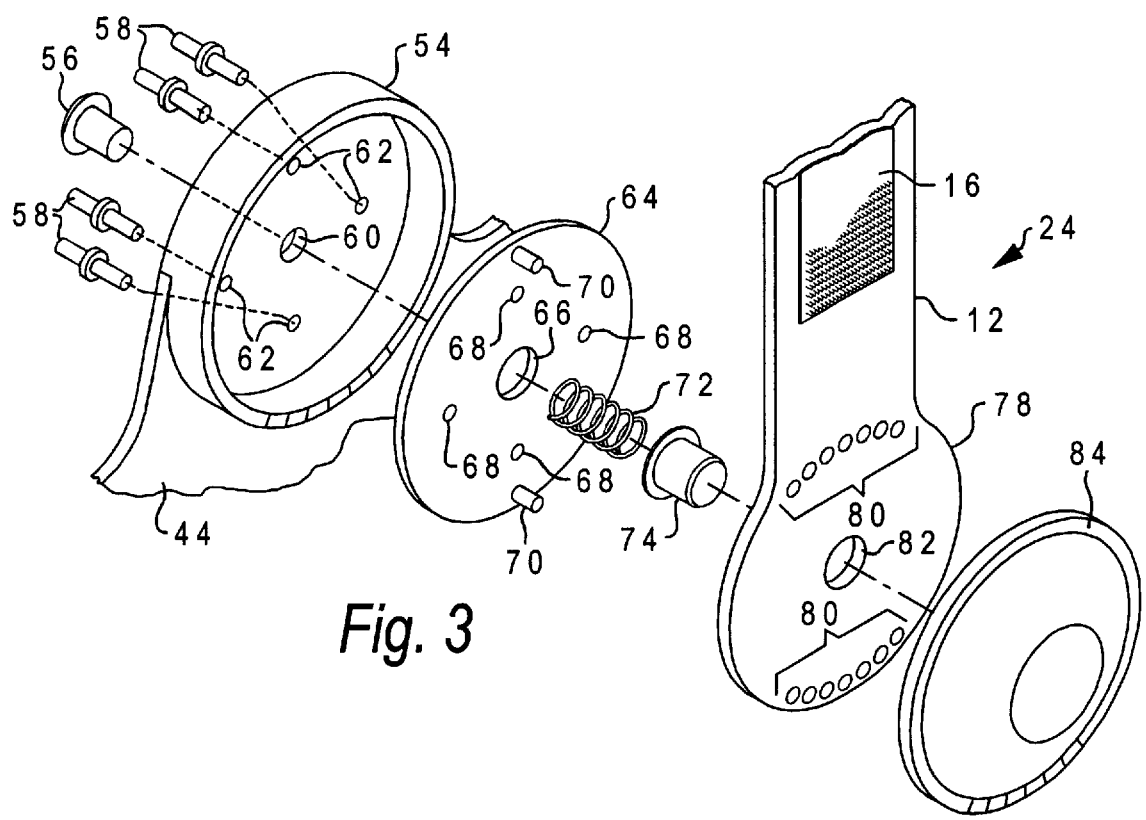
FIG. 3 is an exploded view of a rotatable hinge utilized in the combination night splint and walking boot of the present invention.

With reference now to FIG. 3, there is depicted an exploded view of rotatable hinge 24, which may be utilized in construction of the combination night splint and walking boot 10 of the present invention. Of course, rotatable hinge 26 is constructed in an identical manner. As depicted, a hinge socket 54 is integrally formed as part of raised lip portion 44. Hinge socket 54 receives axle pin 56 through axle aperture 60 and a plurality of position pins 58 through a matching plurality of position pin apertures 62.

Lock plate 64 is also illustrated in FIG. 3. As depicted, lock plate 64 includes a lock plate axle aperture 66 and lock plate position pin apertures 68. Each lock plate position pin 68 is aligned with a position pin aperture 62 within hinge socket 54 and receives a position pin 58, thus prohibiting rotation of lock plate 64.

An important feature of the rotatable hinge of the present invention is the provision of lock pins 70. As depicted, two lock pins 70 are provided and, in a manner which will be explained in greater detail herein, these lock pins may be inserted into a selected lock pin aperture 80 to adjust the angular relationship between leg brace 12 and combination night splint and walking boot 10.

Still referring to FIG. 3, spring 72 and axle pin cap 74 are also provided and are coaxially aligned with axle pin 56 to provide adjustment of rotatable hinge 24 in a manner which will be explained in greater detail herein. Leg brace 12 having hook or loop strip 16 attached thereto, terminates in a brace plate 78 which includes a plurality of lock pin apertures 80 and a brace plate axle aperture 82. Axle pin cap 74 will protrude through brace plate axle aperture 82 and each lock pin 70 will be inserted into a selected one of lock pin apertures 80 to provide fixed angular adjustment as depicted below. Finally, a flexible cap 84 is provided and mounted conventionally to brace plate 78 to protect the mechanisms contained therein and provide means for adjusting rotatable hinge 24, as explained below.

Figure 4:
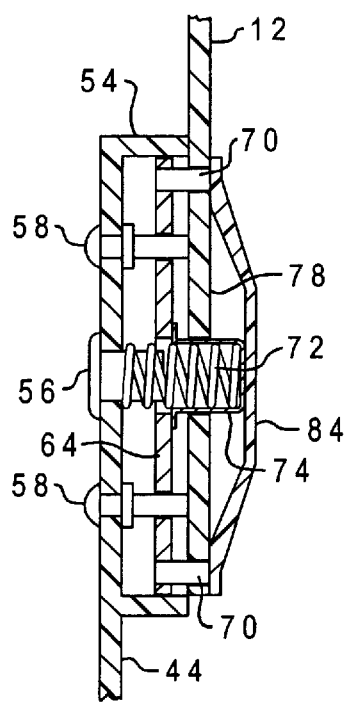
FIG. 4 is a cut-away side view of the rotatable hinge of FIG. 3, in a locked position.

Referring now to FIG. 4, there is depicted a cut-away side view of rotatable hinge 24 of FIG. 3, in a locked position. As depicted herein, position pins 78 prevent rotation of lock plate 64. As illustrated, lock pins 70, mounted to lock plate 64, are each inserted into a lock pin aperture 80 within brace plate 78 and consequently, leg brace 12 is prohibited from rotating with respect to the combination night splint and walking boot 10 of the present invention.

Figure 5:
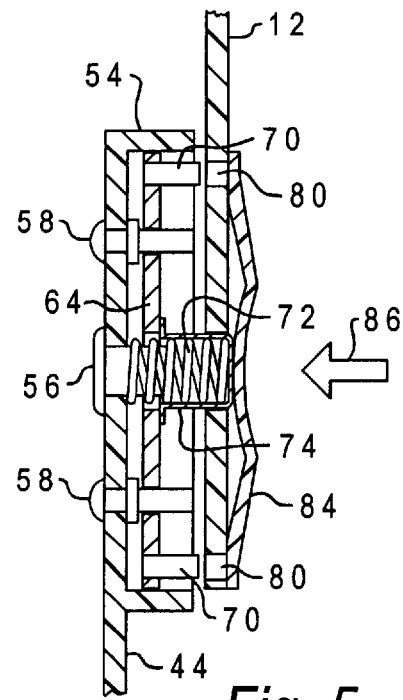
FIG. 5 is a cut-away side view of the rotatable hinge of FIG. 3, in a pivoting position.
Figure 8:
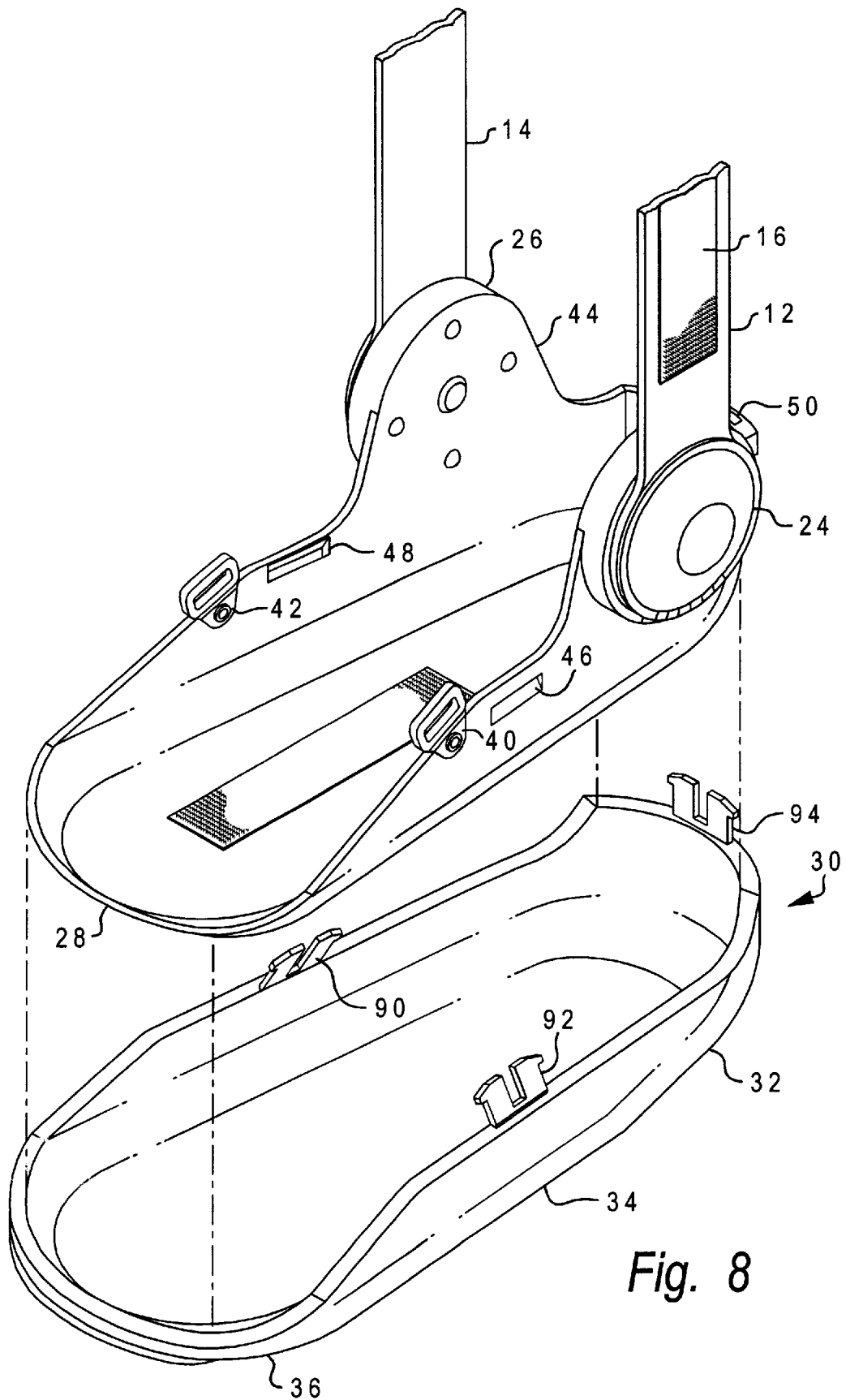
FIG. 8 is an exploded view demonstrating the joining of the night splint portion and walking boot portion of the combination night splint and walking boot of the present invention.

With reference now to FIG. 5, there is depicted a cut-away side view of rotatable hinge 24 of FIG. 3, in a pivoting position. As illustrated in this Figure, flexible cap 84 has been depressed inward in the direction indicated at arrow 86. Axle pin cap 74 compresses spring 72, pushing lock plate 64 further onto each position pin 58. In this position, lock pins 70 are disengaged from lock pin apertures 80 within brace plate 78. While flexible cap 84 remains depressed in the depicted position, leg brace 12 may be rotated with respect to combination night splint and walking boot 10. In the depicted embodiment of the present invention, six lock pin apertures 80 are provided in both the upper and lower region of brace plate 78 and each one is located in order to permit ten (10°) degrees of Dorsi flexion or Plantar flexion of combination night splint and walking boot 10 with respect to leg brace 12. In this manner, the health professional may select a particular orientation to be maintained between the patient's foot and lower leg in accordance with the treatment regimen, which is desired.

Referring now to FIGS. 6A–6C, there are depicted schematic views of rotatable hinge 24 of FIG. 3, demonstrating the aforementioned range of adjustment. As depicted, the positioning of lock pins 70 into selected lock pin apertures 80 may result in a ten (10°) degree Dorsi flexion or ten (10°) degree Plantar flexion. Similarly, in FIG. 6B, a twenty (20°) degree Dorsi flexion or twenty (20°) degree Plantar flexion may be obtained. Finally, as depicted in FIG. 6C, a thirty (30°) degree Dorsi flexion or thirty (30°) degree Plantar flexion may be selected, providing a wide range of treatment options to the health care professional.

With reference now to FIG. 7, there is depicted a perspective view of walking boot attachment 30 of the combination night splint and walking boot 10 of the present invention. As illustrated, walking boot attachment 30 is a sturdy, weight-bearing unit, which includes a heel portion 32, a mid-foot portion 34 and a toe portion 36. As described above, heel portion 32 and toe portion 36 are inclined slightly from the plane defined by mid-foot portion 34 to assist the patient in walking.

Still referring to FIG. 7, as depicted therein, walking boot attachment 30 includes a plurality of mounting tabs, 90, 92 and 94. In the depicted embodiment, each mounting tab 90, 92 or 94, includes a mounting tab slot, 96, 98 and 100. Further, each mounting tab includes a pair of mounting tab ears. Thus, mounting tab 90 includes mounting tab slot 96 and mounting tab ears 102 and 104. Similarly, mounting tab 92 includes a mounting tab slot 98 and mounting tab ears 106 and 108. Finally, mounting tab 94 includes a mounting tab slot 100 and mounting tab ears 110 and 112. Mounting tabs 90, 92 and 94 are preferably constructed of a sufficiently flexible material such that compression of each portion of the mounting tab toward the mounting tab slot will provide sufficient clearance so that the associated mounting tab ears may pass through an associated rectangular mounting tab slot and, once clear, may expand to form a temporary and efficient lock.

With reference now to FIGS. 9 and 10, there are illustrated partial views of the interaction between mounting slots and mounting tabs which may be utilized to join together the combination night splint and walking boot portions of the present invention. As illustrated in FIG. 9, mounting tab 92 has been compressed toward mounting tab slot 98 such that mounting tab ears 106 and 108 have passed through mounting slot 46 and thereafter expanded, forming a rigid bond between walking boot attachment 30 and foot support member 28. Similarly, raised lip portion 44 in FIG. 10 forming the counter around the heel portion of foot support member 28 includes a mounting slot 50 which, in the matter described above, has accommodated mounting tab 94.

Upon reference to the foregoing, those skilled in the art will appreciate that the inventor's herein have provided a lightweight night splint which may be rapidly and efficiently converted to a walking boot while maintaining a desired orientation between the patients foot and lower leg, permitting accommodation of sleep or large periods of inactivity and ambulation.

While the invention has been particularly shown and described with reference to a preferred embodiment, it will be understood by those skilled in the art that various changes in form and detail may be made therein without departing from the spirit and scope of the invention.

What is claimed is:

1. A combination night splint and walking boot comprising:

a foot support member, said foot support member having a thin, flat sole portion extending from a heel area to a toe area and including a raised lip portion forming a counter around the heel area which extends along each side of the thin, flat sole portion;

a plurality of mounting slots disposed within the raised lip portion;

a pair of lower leg braces, each attached at a lower end thereof to said foot support member; and a walking boot attachment, said walking boot attachment having a sturdy weight bearing sole portion and a plurality of mounting tabs adapted to temporarily mate with said plurality of mounting slots wherein a patient may walk while wearing a night splint.

2. The night splint and walking boot according to claim 1, wherein said foot support member is constructed of lightweight plastic material.

3. The night splint and walking boot according to claim 1, wherein said foot support member is constructed of lightweight aluminum material.

4. The night splint and walking boot according to claim 1, wherein each of said plurality of mounting slots is generally rectangular in dimension.

5. The night splint and walking boot according to claim 4, wherein each of said plurality of mounting tabs is slit along one axis and compressible perpendicular to said one axis for insertion into said plurality of mounting slots.

6. The night splint and walking boot according to claim 1, further including at least one strap mounted perpendicularly across said raised lip portion for retaining a human foot.

7. The night splint and walking boot according to claim 1, wherein each of said pair of lower leg braces is attached at a lower end thereof to said foot support member by means of a hinge having a variable mounting angle for adjusting Plantar flexion and Dorsi flexion.

8. The night splint and walking boot according to claim 7, wherein each of said hinges is variable in ten (10°) degree increments from vertical.

9. The night splint and walking boot according to claim 1, wherein each of said pair of lower leg braces includes a strip of hook or loop fastener material along the outer side thereof.

10. The night splint and walking boot according to claim 8, further including at least one strap formed of hook or loop fastener material for wrapping the lower leg between said pair of lower leg braces.

11. The night splint and walking boot according to claim 1, wherein said walking boot attachment includes a heel portion, a mid-foot portion and a toe portion and wherein said toe portion and heel portion are slightly inclined from the plane formed by the mid-foot portion.

\* \* \* \* \*